United States Patent [19]

Fredberg et al.

[11] Patent Number: 5,882,314

[45] Date of Patent: Mar. 16, 1999

[54] AIRWAY GEOMETRY IMAGING

[75] Inventors: Jeffrey J. Fredberg, Sharon; Bruno Louis, Boston, both of Mass.

[73] Assignee: Biomechanics, Inc., Boston, Mass.

[21] Appl. No.: 808,907

[22] Filed: Dec. 17, 1991

[51] Int. Cl.[6] .................................................... A61B 5/08
[52] U.S. Cl. .......................................... 600/529; 600/533
[58] Field of Search ..................................... 128/717, 718, 128/719, 720, 721, 722, 200.24, 204.22, 23, 207.13, 18, 773, 207.14, 600.1, 2, 7, 661.3, 662.3, 774, 780; 600/529, 533

[56] References Cited

U.S. PATENT DOCUMENTS

| | | | |
|---|---|---|---|
| 3,857,385 | 12/1974 | Hampl | 128/720 |
| 4,326,416 | 4/1982 | Fredberg | 734/597 |
| 4,558,708 | 12/1985 | Labuda et al. | |

FOREIGN PATENT DOCUMENTS

| | | |
|---|---|---|
| A 2 672 793 | 2/1991 | France . |
| WO 91/12051 | 8/1991 | WIPO . |

OTHER PUBLICATIONS

M. Cauberghs and KP Vande Woestijne, "Mechanical Properties of the Upper Airway," 1983 pp. 335–342.

Schroder, "Determination of the Geometry of the Human Vocal Tract by Acoustic Measurement", 1967, pp. 1002–1010.

Acoustic measurement of the respiratory system—an acoustic pneumograph, Miyakawa et al., Medical and Biological Engineering and Computing, vol. 14, No. 6, Nov. 1976, pp. 653–659., Stevenage GB.

Microcomputer–based system of calculate respiratory impedance from forced random noise data, Pelle et al., Medical and Biological Engineering and Computing, vol. 24, No. 5, Sep. 1986, pp. 541–544, Stevenage GB.

Instrumentation for Measuring Respiratory Impedance by Forced Oscillations, Pimmell et al., IEEE Transactions on BME, vol. 24, No. 2, Mar. 1977, pp. 89–93, New York, US.

Dec. 4, 1995 EPO Supplementary European Search Report Application No. 92923438.3—PCT/US9209236.

PCT International Search Report dated 17 Sep. 1993.

M. Cauberghs and K.P. Van de Woestijne, Mechanical Properties of the Upper Airway, 1983, pp. 335–342.

J.Y. Chung and D.A. Blaser, Transfer Function Method of Measuring In–Duct Acoustic Properties. I. Theory, 1980, pp. 907–908, 910–913.

J.Y. Chung and D.A. Blaser, Transfer Function Method of Measuring In–Duct Acoustic Properties. II. Experiment 1980, pp. 914–921.

K.P. Van de Woestijne, H. Franken, M. Cauberghs, F.J. Landser and J. Clement, A Modification of the Forced Oscillation Technique, >1976, pp. 655–660.

A.F. Seybert and D.F. Ross, Experimental Determination of Acoustic Properties Using a Two–Microphone Random–Excitation Technique, 1976, pp. 1362–1370.

*Primary Examiner*—Frances Jaworski
*Attorney, Agent, or Firm*—Fish & Richardson P.C.

[57] ABSTRACT

Apparatus provides an output signal characteristic of the geometry of a confined volume. There is a conduit with an open first end for exchanging acoustical energy with the confined volume. An electroacoustical transducer is coupled to the conduit for launching acoustical energy into the conduit towards the opening in the confined volume producing an incident wave and a reflected wave to form a transient wave field representative of the geometry of the confined volume. At least first and second pressure-wave-sensing transducers are mounted along the length of the conduit in spaced relationship for providing first and second transduced signals representative of the transient wave field at spaced locations in the conduit. A processor processes the first and second transduced signals to provide an output signal characteristic of the geometry of the confined volume.

22 Claims, 6 Drawing Sheets

AIRWAY GEOMETRY IMAGING

This invention relates in general to imaging airway geometry and more particularly concerns noninvasively obtaining a signal representative of the cross-sectional area of an airway (e.g., oral, nasal, or pulmonary) of a subject (e.g., a person or an animal) using multiple spaced electroacoustical transducers.

A one-dimensional image of the cross-sectional area of an airway as a function of axial position along the airway may be determined from acoustic reflections measured by a single electro-acoustic transducer placed in a position remote from the airway opening. This image is referred to as an area-distance function and is represented by A(x) where x is the axial position along the airway.

Knowledge of the area-distance function, A(x), is useful in the diagnosis of pathologies associated with oral airways, larynx, pulmonary airways, and nasal airways, for example. These pathologies include but are not limited to obstructive sleep apnea, asthma, obstructive pulmonary disease, tracheal stenosis, and nasal septum deviation. Accurate information about the area-distance function is also useful in the study of airway growth and its disruption and sequelae of bronchopulmonary dysplasia in children, for example.

One approach toward using a single electro-acoustic transducer is described in U.S. Pat. No. 4,326,416 granted Apr. 27, 1982, to Jeffrey J. Fredberg entitled ACOUSTIC PULSE RESPONSE MEASURING. A two-transducer approach is described in a paper of M. R. Schroeder entitled "Determination of the Geometry of the Human Vocal Tract by Acoustic Measurements" in J. Acoust. Soc. Am. 41(4), 1002–10 (1967).

According to the invention there is apparatus for providing an output signal characteristic of the geometry of a confined volume including a conduit for exchanging acoustical energy with the confined volume. The conduit has an open first end in communication with an opening in the confined volume. A transducer, such as a loudspeaker, is coupled to the conduit for launching acoustical energy into the conduit producing an incident wave towards the opening in the confined volume and a reflected wave to form a transient wave field in the conduit representative of the geometry of the confined volume. At least first and second pressure wave sensing transducers, such as microphones, mounted along the length of the conduit in spaced relationship provide first and second transduced signals representative of the transient wave field. A processor processes the first and second transduced signals to provide an output signal characteristic of the geometry of the confined volume, such as the cross-sectional area of the confined volume as a function of the distance from the opening in the confined volume.

The process according to the invention includes connecting the open first end of the conduit to an opening in the confined volume, delivering acoustical energy into the conduit to provide incident and reflected waves that form the transient wave field in the conduit, transducing acoustic energy at spaced locations along said conduit to provide first and second transduced signals representative of said transient wave field at spaced locations in the conduit, and processing said first and second transduced signals to provide an output signal representative of the geometry of said confined volume.

The invention provides signals representative of airway geometry without calibration in apparatus that is relatively small and portable. The invention may be used for diagnostic and screening purposes in a confined area such as a laboratory, a doctor's office, a place of work, and at bedside. Additionally, the invention requires little or no cooperation by the subject being tested, facilitating its use in pediatric applications.

Other features, objects, and advantages of the invention will become apparent from the following detailed description and from the claims when read in connection with the accompanying drawings in which:

Figure 1:
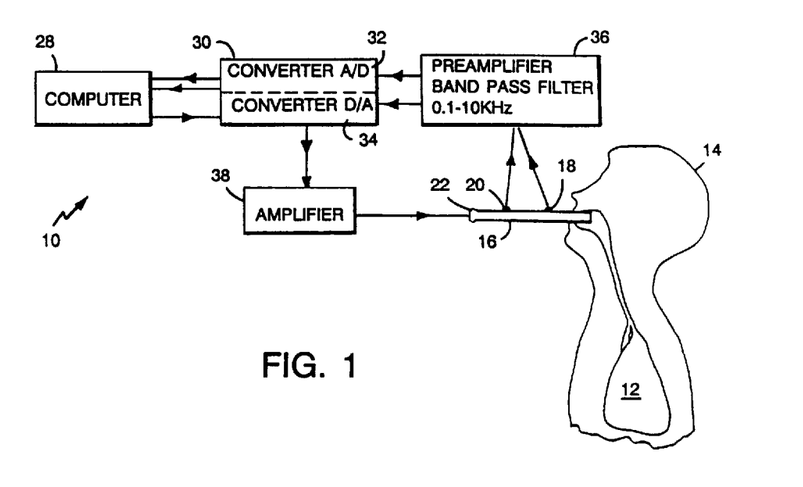
FIG. 1 is a combined block-pictorial diagram illustrating the logical arrangement of a noninvasive, spaced-transducer system for imaging airway geometry according to the invention.

Referring now to FIG. 1, a spaced-transducer system 10 for noninvasively obtaining a signal representative of the cross-sectional area of an airway 12 (e.g., a pulmonary airway) of a subject 14 (e.g., a person or an animal) includes a tube 16 with a diameter typically of 1.2 cm and a length typically of 15.0 cm. Two spaced pressure transducers 18, 20 (such as Endevco series 8510 B microphones) are mounted in tube 16 with their pressure sensing heads flush with the inner tube wall in order to reduce parasitic acoustic reflection. A loudspeaker 22 (such as Sony model MDR 434) is connected to one end of the tube 16. The other end of tube 16 is inserted in the airway opening of the subject. Transducers 18, 20 are typically separated by 10.25 cm, and transducer 18 is located typically 2.0 cm from the airway opening.

A microcomputer 28 (such as Compuadd model 320 with an Intel 80386 microprocessor operating at 20 MHz) is coupled to converter module 30 having a 12-bit analog-to-digital (A/D) converter 32 with a sampling period typically of 24.0 $\mu$s and a 12-bit digital-to-analog (D/A) converter 34 coupled to preamplifier 36 typically with a band-pass filter having a passband from 0.1 kHz to 10.0 kHz (such as Tektronix model AM 502) that is coupled to transducers 18 and 20. D/A converter 34 is coupled to loudspeaker 22 through amplifier 38.

Figure 2:
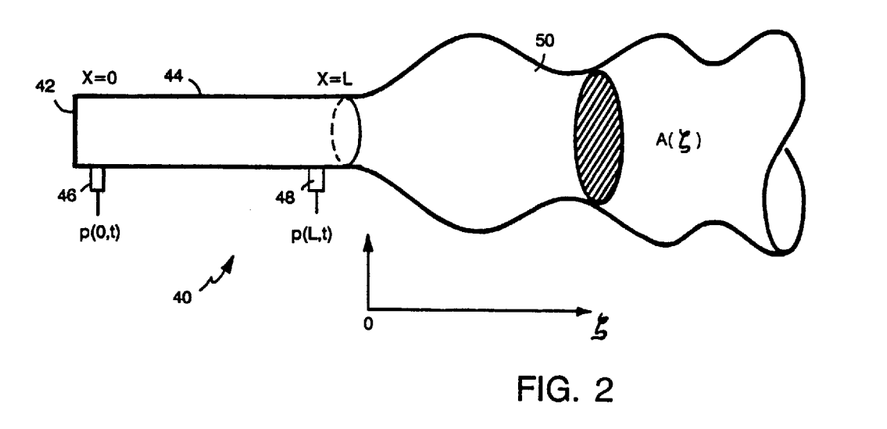
FIG. 2 is a simplified diagram illustrating the spaced-transducer system.

The mode of operation will now be described. Referring to FIG. 2, a simplified assembly 40 includes loudspeaker 42, tube 44 of length L, first transducer 46 located at x=0 where x is the axial position along tube 44, second transducer 48 located at x=L, and airway 50 (e.g., an oral, nasal, or pulmonary airway) of a subject.

Loudspeaker 42 launches a one-dimensional essentially lossless acoustic wave into tube 44. The launched incident wave travels through tube 44 and into airway 50. A reflected wave, or echo, representative of gradients in the acoustic impedance in the airway then propagates back through tube 44 towards loudspeaker 42. Transducers 46 and 48 provide transduced electrical signals representative of the incident and reflected waves for processing by computer 28 (FIG. 1).

Referring to FIG. 1, microcomputer 28 generates a digital probe signal converted to an analog signal by D/A converter 34, and amplified by amplifier 38 to drive loudspeaker 22 and launch the incident probe acoustic wave. The transduced outputs from transducers 46 and 48 are bandpass filtered by preamplifier 36 and then converted by A/D, converter 32 into digital signals. Microcomputer 28 stores these digital signals.

Microcomputer 28 processes these stored digital signals to provide an output signal A(x), i.e., a one-dimensional image of the cross-sectional area of airway 50 as a function of axial position, x, along airway 50. Computer 28 preferably processes these signals in accordance with the Ware-Aki algorithm ("Continuous and Discrete Inverse-Scattering Problems in a Stratified Elastic Medium. I. Plane Waves at Normal Incidence", J. Acoust. Soc. Am., 54, 4, 911–921, 1969, incorporated herein by reference) to provide the area distance function, A(x), from the impulse response of airway 50, h(t). The relationship between the pressure field and h(t) may be derived as follows. The pressure field within the tube in the domain $0 \leq x \leq L$ can be described as the superposition of two one-dimensional waves propagating with the same wave speed but in opposite directions as given by $$p(x,t)=P_r(x,t)+p_1(x,t) \qquad (1)$$

where t is time, $p_r$ is the incident wave propagating to the right (i.e., from x=0 towards x=L), and $p_1$ is the reflected wave propagating to the left (i.e., from x=L towards x=0). The pressure conditions at x=0 and x=L are given by $$p_1(L,t)=P_r(L,t)*h(t) \qquad (2)$$

and $$p_r(0,t)=p_1(0,t)*s(t) \qquad (3)$$

where s(t) is the impulse response of the loudspeaker and * denotes the convolution operation. Given that a one-way propagation delay is $\tau=L/v$ where v is the velocity of sound, the following relationships exist:

$$p_1(0,t)=p_1(L,t-\tau) \qquad (4)$$

$$p_r(L,t)=p_r(o,t-\tau). \qquad (5)$$

Equations (1) through (5) may be combined by mathematical techniques well-known in the art (e.g., the Fourier transform, the inverse Fourier transform, and algebra) to yield $$h(t)*\{p(0,t)-p(L,t-\tau)\}=p(L,t-\tau)-p(0,t) \qquad (6)$$

and $$h(t)*s(t)=\delta(t-2\tau). \qquad (7)$$

Equation (7) indicates that both waves propagate with an equal, non-zero delay. In equation (7), the symbol δ denotes the well-known impulse function which is sometimes called the delta function. Equation (6) identifies the relationship between the pressure field and h(t).

Equation (6) may be discretized by the Riemann sum approximation to yield $$h(n\Delta t)=\{1/p(0,0)\}\{p(L,(m+n)\Delta t)-p(0,n\Delta t)\}-\{\Sigma h((n-k)\Delta t)/p(0,0)\}\{p(0,k\Delta t)-p(L,(k-m)\Delta t)\} \qquad (8)$$

where $\Delta t$ is the sampling duration of the time discretization, n is the set of integers 1,2,3,etc., m is an integer such that $\tau=m\Delta t$, p(0,0) denotes the first non-zero pressure value at x=0, k is the index of summation, and the lower and upper limits of summation are, respectively, k=1 and k=n.

In brief summary, microcomputer 28 processes the stored digital data signals representative of the transduced signals from the spaced-transducers to provide a signal representative of the impulse response of airway 50, h(t), according to equation (8). Microcomputer 28 then processes the signal h(t) in accordance with the Ware-Aki algorithm to provide a signal, A(x), representative of the geometry of airway 50.

The wave propagation in tube 44 may be assumed lossless, tube 44 being shown free of sound-absorbing or acoustic energy-absorbing material. The early portions of the transduced pressures at x=0 and x=L are then identical except for the propagation delay t. Microcomputer 28 may determine the propagation delay by minimizing mean square differences between the transduced signals in the early part of their respective transients. The relative gain of the transducers may be determined in a similar manner. To obtain sufficient time resolution, microcomputer 28 preferably interpolates the transduced signals to achieve an effective sampling period of 0.75 $\mu$s (i.e., $\Delta t=0.75$ $\mu$s).

Equation (8) requires preferably the propagation delay to be an integral multiple of the sampling period $\Delta t$, i.e., $\tau=m\Delta t$. Microcomputer 28 preferably interpolates and resamples digitized transduced signals such that the propagation delay corresponds to 24 time steps, i.e., $\tau=24\Delta t$. This value of the propagation delay corresponds to a spatial step increment of about 0.2 cm.

In providing h($\Delta t$) in accordance with equation (8), the first non-zero pressure value p(0,0) is preferably larger than some minimal threshold value to maintain stability. The pressure values occurring before this first threshold pressure are initially neglected to obtain a first approximation of h(t). To deemphasize errors that may be introduced by the threshold it is advantageous to provide a corrected h($\Delta t$) characterized by increased stability and accuracy by convolving the first approximation of h(t) with the digitized pressure values occurring prior to the first non-zero pressure (i.e., the pressure values that were initially neglected).

Microcomputer 28 then preferably bandpasses the sequence of discrete values h(n$\Delta t$) that represents the impulse response of the airway h(t) with a digital, linear-phase, finite impulse response (FIR) filter having a passband from 0.01 kHz to 9 kHz to attenuate physiologic noise associated with breathing, artifacts associated with airway wall nonrigidity, instability of the impulse response, h(t), and artifacts associated with acoustic cross-modes.

Microcomputer 28 then processes the corrected h($\Delta t$) signal in accordance with the Ware-Aki algorithm to provide an output signal representative of the area-distance function, A(x), of the airway graphically represented.

Figure 3:
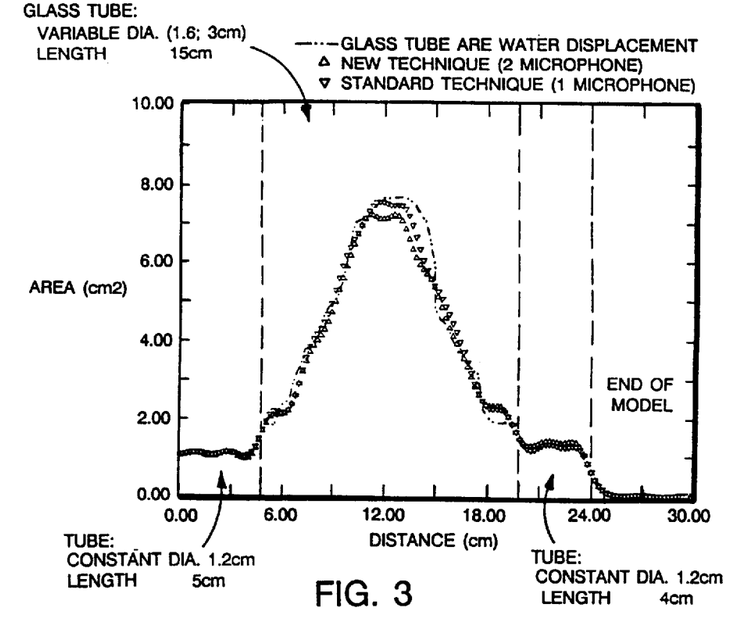
FIG. 3 shows plots of an area-distance function of a glass tube with variable diameter as determined by the dual-transducer system, a water displacement method, and a single-transducer system.

An exemplary embodiment of the invention substantially as shown in FIG. 1 provided a signal characteristic of the area-distance function of an axis-symmetric glass tube with variable diameter and a known area-distance function. FIG. 3 is a graphical representation of this signal compared with corresponding signals obtained by (1) a water displacement method and (2) a single-transducer system of the type described in U.S. Pat. No. 4,326,416.

The water displacement method involved gradually injecting water into a model/cast by a calibrated syringe and measuring the incremental relationship of water column height to water volume injected with a pressure transducer. The cross-sectional area of the water plane is equal to the volume increment divided by the height increment.

The single-transducer system was an existing noninvasive system for obtaining the cross-sectional area of an airway that included a tube with a diameter of approximately 5.0 cm and a minimum length of about 1.0 m; a single pressure transducer mounted in the tube; a sound source located in approximately the middle of the tube; and equipment to generate the sound, process the data recorded by the transducer, and display the processed data.

In FIG. 3, the origin of the distance axis corresponds to the location of the second transducer, i.e., x=L in FIG. 2. All three measured functions correspond substantially to the known area-distance function of the glass tube.

Figure 4:
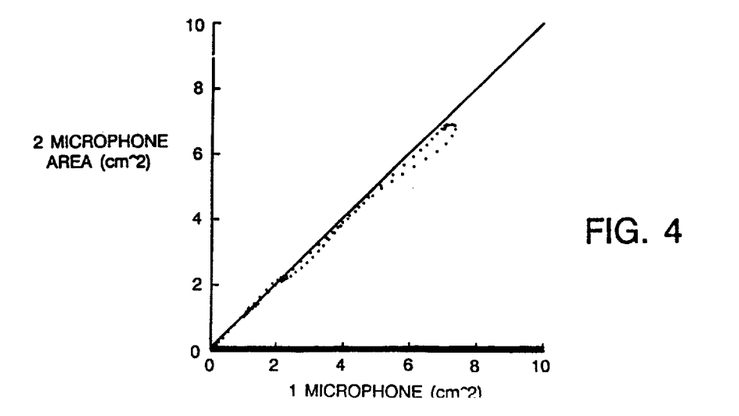
FIG. 4 is a comparison between the dual-transducer system and the single-transducer system.

Referring to FIG. 4, there is shown a graphical representation of departures from correspondence between the measurements of the system of FIG. 1 and the prior art single-transducer system. The correlation coefficient is above 0.998.

Figure 5:
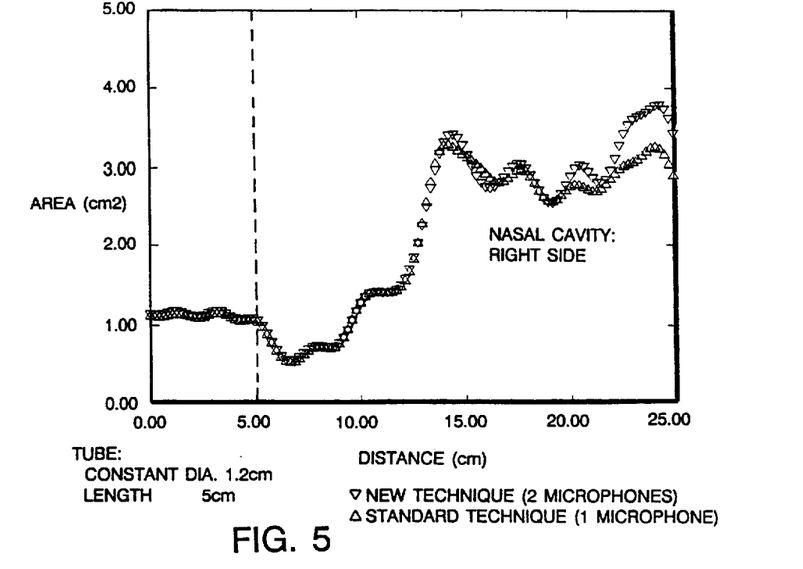
FIGS. 5 and 6 show plots of an area-distance function of the right and left sides of a nasal cavity cast as determined by the dual-transducer system and the single-transducer system, respectively.
Figure 6:
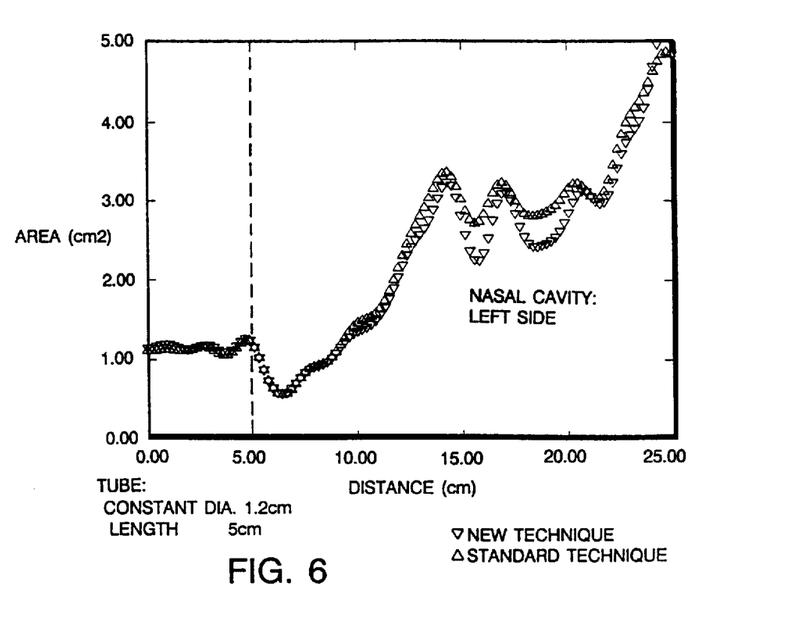
Figure 7:
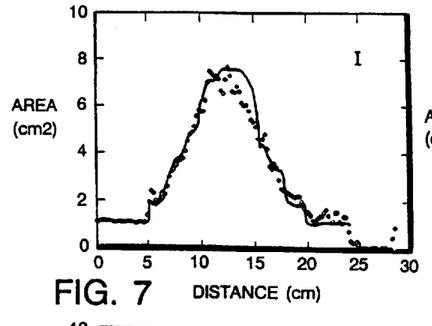
FIGS. 7, 8, 9, and 10 illustrate the effects of using a threshold to identify a first non-zero pressure value in computing the impulse response of the airway.

The system according to the invention and the prior art single-transducer system also provided signals representative of the area-distance function of a nasal cavity of a person. During the measurements, the person breathed slowly and spontaneously through the mouth. FIGS. 5 and 6 show these functions for right and left nasal cavities, respectively. As in FIG. 3, the origin of the distance axis corresponds to the location of the second transducer, i.e., x=L in FIG. 2. The function signals are substantially the same through 10 cm.

Figure 8:
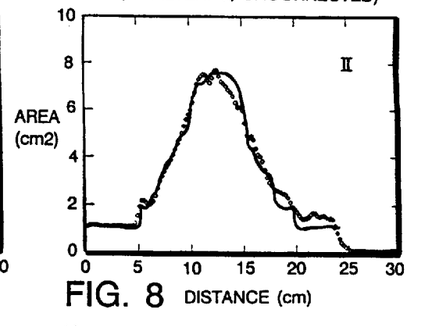
Figure 9:
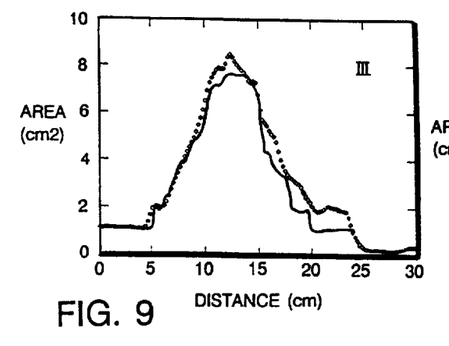
Figure 10:
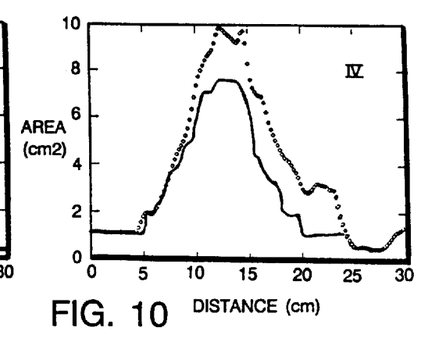
Figure 11:
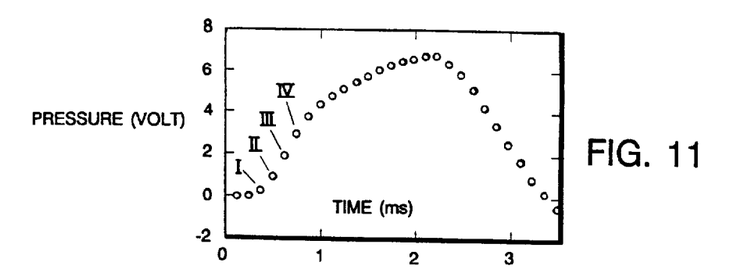
FIG. 11 is a plot of a pressure wave incident on the airway, various values of the pressure threshold being indicated on the plot.

Referring to FIGS. 7–10, there are shown graphical representations of area as a function of distance using the data represented in FIG. 3 for comparing area function through water displacement compared with measurements according to the invention for threshold values I, II, III and IV, respectively, of FIG. 11 graphically representing pressure as a function of time. Closest correspondence between the area function through water displacement and according to the invention is shown in FIG. 8 using threshold level II.

Figure 12:
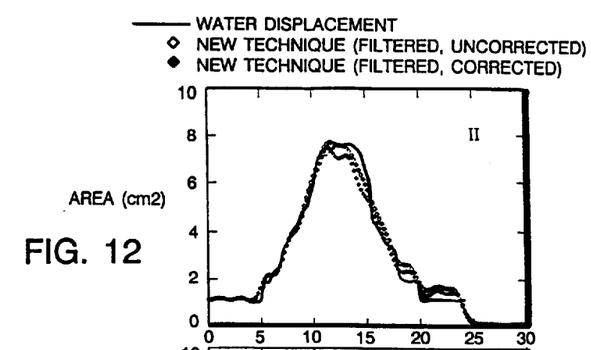
FIGS. 12, 13, and FIG. 14 are plots of the area-distance function of the glass tube.
Figure 13:
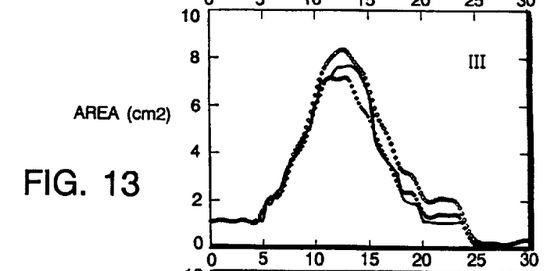
Figure 14:
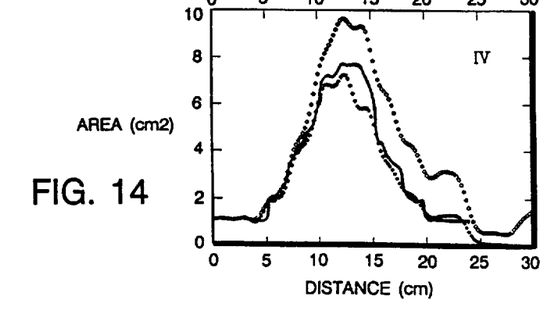

Referring to FIGS. 12, 13 and 14, there are shown graphical representations of the area functions provided according to the invention compared with the area function derived from water displacement based on the impulse response filtered, but uncorrected, and the corrected impulse response filtered for threshold values II, III and IV, respectively.

It was discovered that the first non-zero pressure threshold is preferably approximately 100 times larger than the "noise floor" created by all noise sources combined to achieve adequate stability and accuracy.

Figure 15:
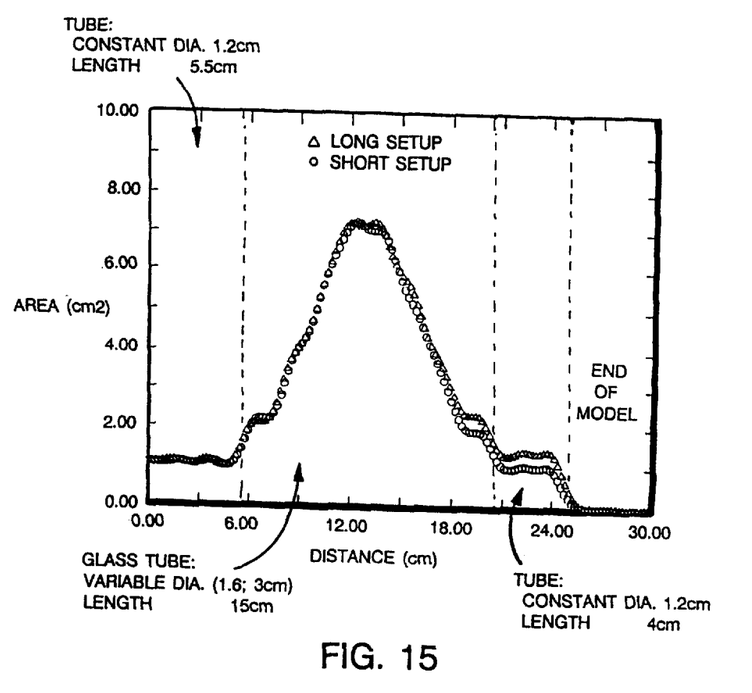
FIG. 15 shows plots of the area-distance function of the glass tube with variable diameter as determined by a dual-transducer system with a 15 cm tube and a dual-transducer system with a 10 cm tube.

Referring to FIG. 15, there is shown the area-distance function of an axially-symmetric glass tube with variable diameter provided by the invention with 15 cm (long setup) and 10 cm long (short setup) tubes, respectively. As in FIGS. 3 and 5–10, the origin of the distance axis corresponds to the location of the second transducer (i.e., x=L in FIG. 2); however, to obtain the same distance origin, the function provided using the long tube was shifted by 0.5 cm. These results show that the invention may provide good results with different tube lengths.

Figure 16:
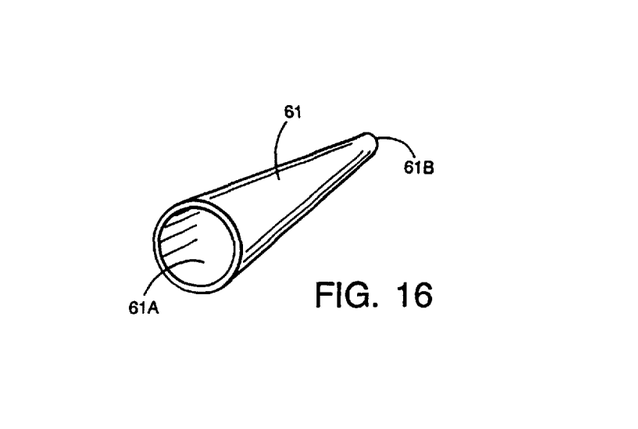
FIG. 16 illustrates a disposable nasal coupling device.

Referring to FIG. 16 there is illustrated a disposable nasal coupling device 61 having an input end 61A that attaches to the ouput end of tube 16 and an output end 61B for insertion into a nostril. Nasal coupling device 61 may have output ends of different sizes for snug engagement with the inside of nostrils of different sizes. Its internal area contour is such that impedance matching between subject and apparatus is maintained with maximum acoustic energy transmission. Similarly there may be disposable mouth coupling devices with output ends of different sizes for snugly engaging mouths of different sizes.

Other embodiments are within the following claims.

For example, tube 16 (FIG. 1) could be 1.2 cm in diameter and 10 cm in length. In this case, the two transducers are preferably separated by 3.0 cm but transducer 18 is still located 2.0 cm from the airway opening. With the 10 cm tube, the propagation delay, $\tau$, is made to correspond to seven time steps, i.e., $\tau=7\Delta t$. This value of the propagation delay corresponds to a spatial step increment of about 0.2 cm.

Also, an algorithm other than the Ware-Aki algorithm could be used to uniquely determine the area-distance function, $A(x)$, of the airway from $h(t)$. Also, algorithms other than equation (8) above could be used to determine $h(t)$ from the pressure field.

The attached appendix sets forth steps in a program for practicing the invention in a specific embodiment.

Other embodiments are within the claims.

What is claimed is:

1. Apparatus for providing an output signal characteristic of the geometry of a confined volume comprising, a conduit that provides a substantially lossless wave provagation medium for exchanging acoustical energy with said confined volume, said conduit having an open first end adapted for communication with an opening in said confined volume and a second end separated from said first end by the conduit length, a launching transducer coupled to said conduit for launching acoustical energy into said conduit producing an incident wave towards said opening in said confined volume and a reflected wave to form a wave field in said conduit representative of the geometry of said confined volume, at least first and second pressure-wave-sensing transducers mounted along said conduit length in spaced relationship for providing first and second transduced signals representative of said wave field, and a processor coupled to said first and second pressure-wave-sensing transducers for processing said first and second transduced signals to provide said output signal characteristic of the geometry of said confined volume, wherein said confined volume is characterized by cross-sectional area as a function of distance from said opening in said confined volume and said processor provides as said output signal an area signal that is characteristic of the cross-sectional area of said confined volume as a function of the distance from said opening in said confined volume.

2. Apparatus as recited in claim 1 wherein said conduit is constructed and arranged so that said first end is formed to snugly engage an opening to an airway of an animal which airway comprises said confined volume.

3. Apparatus as recited in claim 2 wherein said conduit is constructed and arranged so that said first end is formed to snugly engage an opening to an airway of a human which airway comprises said confined volume.

4. Apparatus as recited in claim 2 wherein said conduit is constructed and arranged so that said first end is formed to snugly engage an opening to a pulmonary airway comprising said airway.

5. Apparatus as recited in claim 4 wherein said conduit is constructed and arranged so that said first end is formed to snugly engage an opening to a nasal airway comprising said airway.

6. Apparatus as recited in claim 4 wherein said conduit is constructed and arranged so that said first end is formed to snugly engage an opening to an oral airway comprising said airway.

7. Apparatus as recited in claim 1 wherein said conduit is less than 15 cm in length.

8. Apparatus as recited in claim 7 wherein said conduit is of the order of 10 cm in length.

9. Apparatus as recited in claim 8 wherein said first and second pressure-wave-sensing transducers are separated by of the order of 3.0 cm.

10. Apparatus as recited in claim 1 wherein said conduit is of the order of 15 cm in length.

11. Apparatus as recited in claim 10 wherein said first and second pressure-wave-sensing transducers are separated by of the order of 10.25 cm.

12. A method for imaging a confined volume comprising:
connecting an open first end of a conduit that provides a substantially lossless wave propagation medium to an opening in said confined volume;
propagating acoustical energy inside said conduit, through said open first end, and into said confined volume through said opening to establish a pressure field in said conduit representative of said confined volume;
transducing acoustic wave field parameters of said pressure field at at least two spaced locations along said conduit; and
processing said transduced parameters to provide an output signal representative of said confined volume,
wherein said confined volume is characterized by cross-sectional area as a function of distance from said opening in said confined volume and said output signal is representative of the cross-sectional area of said confined volume as a function of the distance from said opening in said confined volume.

13. Apparatus for providing an output signal indicative of the geometry of a confined volume comprising,
a conduit for exchanging acoustical energy with said confined volume,
said conduit having an open first end adapted for communication with an opening in said confined volume and a second end separated from said first end by the conduit length,
a launching transducer coupled to said conduit for launching acoustical energy into said conduit producing an incident wave towards said opening in said confined volume and a reflected wave on a wave field in said conduit representative of the geometry of said confined volume,
at least first and second pressure-wave-sensing transducers mounted along said conduit length in spaced relationship for providing first and second transduced signals representative of said wave field, and
a processor coupled to said first and second pressure-wave-sensing transducers for processing said first and second transduced signals to provide said output signal indicative of the geometry of said confined volume,
wherein said confined volume is coupled to said open first end through a body passage input and wherein said conduit comprises,
a tube and a disposable device having an output end for snug engagement with said body passage input and an input end for snug engagement with said tube with good acoustic impedance matching and energy transmission.

14. Apparatus for providing an output signal characteristic of the geometry of a confined volume comprising,
a conduit for exchanging acoustical energy with said confined volume,
said conduit having an open first end adapted for communication with an opening in said confined volume and a second end separated from said first end by the conduit length,
a launching transducer coupled to said conduit for launching acoustical energy into said conduit producing an incident wave towards said opening in said confined volume and a reflected wave on a wave field in said conduit representative of the geometry of said confined volume,
at least first and second pressure-wave-sensing transducers mounted along said conduit length in spaced relationship for providing first and second transduced signals representative of said wave field, and
a processor coupled to said first and second pressure-wave-sensing transducers for processing said first and second transduced signals to provide said output signal characteristic of the geometry of said confined volume,
wherein said confined volume is coupled to said open first end through a nostril having an input and wherein said conduit comprises,
a tube and a disposable device having an output end sized for snug engagement with the input of said nostril and an input end for snug engagement with said tube with good acoustic impedance matching and energy transmission.

15. Apparatus for providing an output signal characteristic of the geometry of a confined volume comprising,
a conduit that provides a substantially lossless wave propagation medium for exchanging acoustical energy with said confined volume,
said conduit having an open first end adapted for communication with an opening in said confined volume and a second end separated from said first end by the conduit length,
a launching transducer coupled to said conduit comprising means for launching acoustical energy into said conduit producing a first wave traveling towards said opening in said confined volume and a second wave traveling away from said opening toward said second end to form a wave field in said conduit representative of the geometry of said confined volume,
at least first and second pressure-wave-sensing transducers mounted along said conduit length in spaced relationship for providing first and second transduced signals representative of said wave field,
and a processor coupled to said first and second pressure-wave-sensing transducers including means for processing said first and second transduced signals in accordance with an algorithm that takes into account said first wave and said second wave to provide said output signal characteristic of the geometry of said confined volume.

16. A method for imaging a confined volume comprising,
connecting an open first end of a conduit that provides a substantially lossless wave propagation medium to an opening in said confined volume, propagating acoustical energy inside said conduit through said open first end and into said confined volume through said opening to establish to produce a first wave traveling towards said opening in said confined volume and a second wave traveling away from said opening towards said second end to form a wave field in said conduit representative of the geometry of said confined volume, transducing acoustic wave field parameters of said wave field at at least two spaced locations along said conduit to provide first and second transduced signals representative of said wave field, and processing said first and second transduced signals in accordance with an algorithm that takes into account said first wave and said second wave to provide an output signal representative of a characteristic of said confined volume.

17. A method in accordance with claim 12 wherein said output signal is representative of the cross-sectional area of said confined volume as a function of the distance from said opening in said confined volume.

18. Apparatus for providing an output signal characteristic of the geometry of a confined volume comprising, a conduit for exchanging acoustical energy with said confined volume, said conduit having an open first end adapted for communication with an opening in said confined volume and a second end separated from said first end by the conduit length, a launching transducer coupled to said conduit for launching acoustical energy into said conduit producing an incident wave towards said opening in said confined volume and a reflected wave to form a wave field in said conduit representative of the geometry of said confined volume, at least first and second pressure-wave-sensing transducers mounted along said conduit length in spaced relationship for providing first and second transduced signals representative of said wave field, and a processor coupled to said first and second pressure-wave-sensing transducers for processing said first and second transduced signals to provide said output signal characteristic of the geometry of said confined volume, wherein said confined volume is characterized by cross-sectional area as a function of distance from said opening in said confined volume and said processor provides as said output signal an area signal that is characteristic of the cross-sectional area of said confined volume as a function of the distance from said opening in said confined volume, wherein said conduit is less than or equal to 15 cm in length.

19. Apparatus in accordance with claim 18 wherein said conduit is substantially 15 cm in length.

20. Apparatus in accordance with claim 19 wherein said first and second pressure wave sensing electroacoustical transducers are separated by substantially 10.52 cm.

21. Apparatus in accordance with claim 18 wherein said conduit is substantially 10 cm in length.

22. Apparatus in accordance with claim 21 wherein said first and second pressure wave sensing transducers are separated by substantially 3.0 cm.

* * * * *